United States Patent [19]

Henderson

[11] Patent Number: 5,207,773

[45] Date of Patent: May 4, 1993

[54] TEETH CLEANING APPARATUS

[76] Inventor: Doug Henderson, 1390 California Ave., Turlock, Calif. 95380

[21] Appl. No.: 618,110

[22] Filed: Nov. 26, 1990

[51] Int. Cl.$^5$ .............................................. A61C 5/00
[52] U.S. Cl. .................................... 132/322; 132/323
[58] Field of Search ............... 132/322, 323, 324, 325, 132/326, 327, 309; 128/66; 433/126, 131

[56] References Cited

U.S. PATENT DOCUMENTS

| | | | |
|---|---|---|---|
| 1,989,895 | 2/1935 | Van Gilder | 132/323 |
| 2,450,635 | 10/1948 | Dembenski | 132/325 |
| 3,421,524 | 1/1969 | Waters | 132/322 |
| 3,534,745 | 10/1970 | Waters | 132/322 |
| 3,759,274 | 9/1973 | Warner | 132/322 |
| 4,005,721 | 2/1977 | Yasumoto | 132/325 |
| 4,245,658 | 1/1981 | Lecouturier | 132/322 |
| 4,326,549 | 4/1982 | Hinding | 132/322 |
| 4,586,521 | 5/1986 | Urso | 132/322 |
| 4,883,080 | 11/1989 | Lang | 132/322 |

*Primary Examiner*—John J. Wilson
*Attorney, Agent, or Firm*—Irving M. Weiner; Joseph P. Carrier; Pamela S. Burt

[57] ABSTRACT

The present invention relates to teeth cleaning apparatus comprising a handle unit having a casing with a motor disposed therein, and at least one disposable floss applicator unit adapted to be selectively, drivably connected to the handle unit. The floss applicator unit includes a casing with a floss applicator tip, a floss tube rotatably disposed within the applicator casing and a quantity of floss provided thereon. The motor has a rotatable output shaft which projects outwardly of the handle casing and is adapted to be securely, coaxially received within one end of the floss tube when the floss applicator unit is connected to the handle unit such that the floss tube will rotate together with the output shaft when the motor is actuated.

18 Claims, 3 Drawing Sheets

FIG. 1
FIG. 2
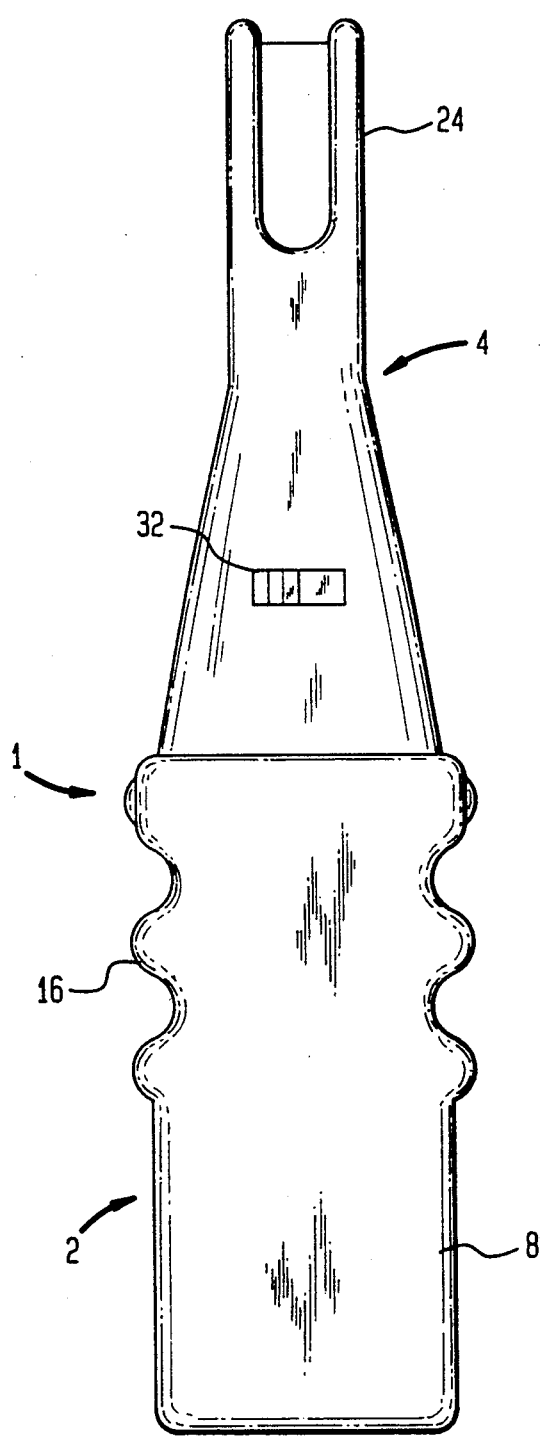
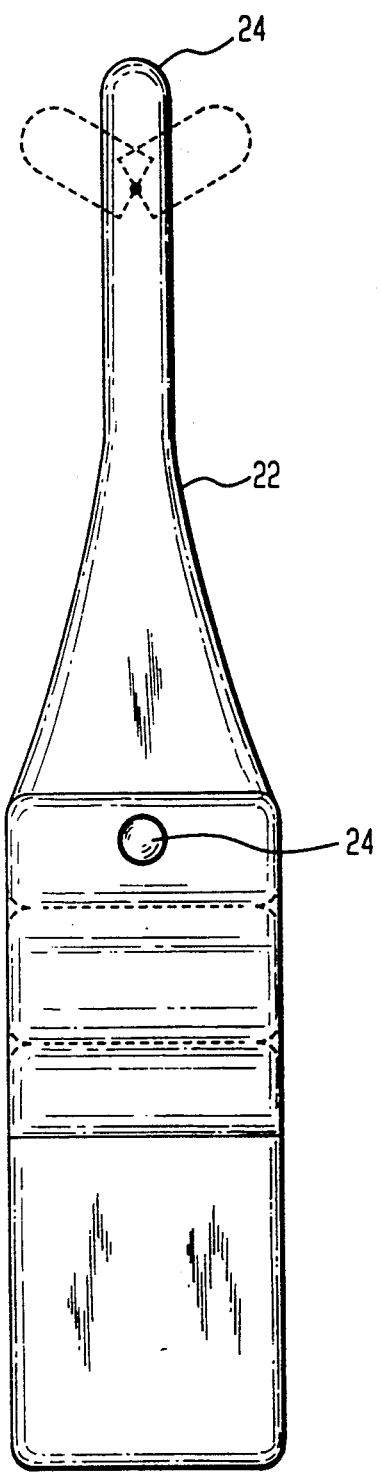

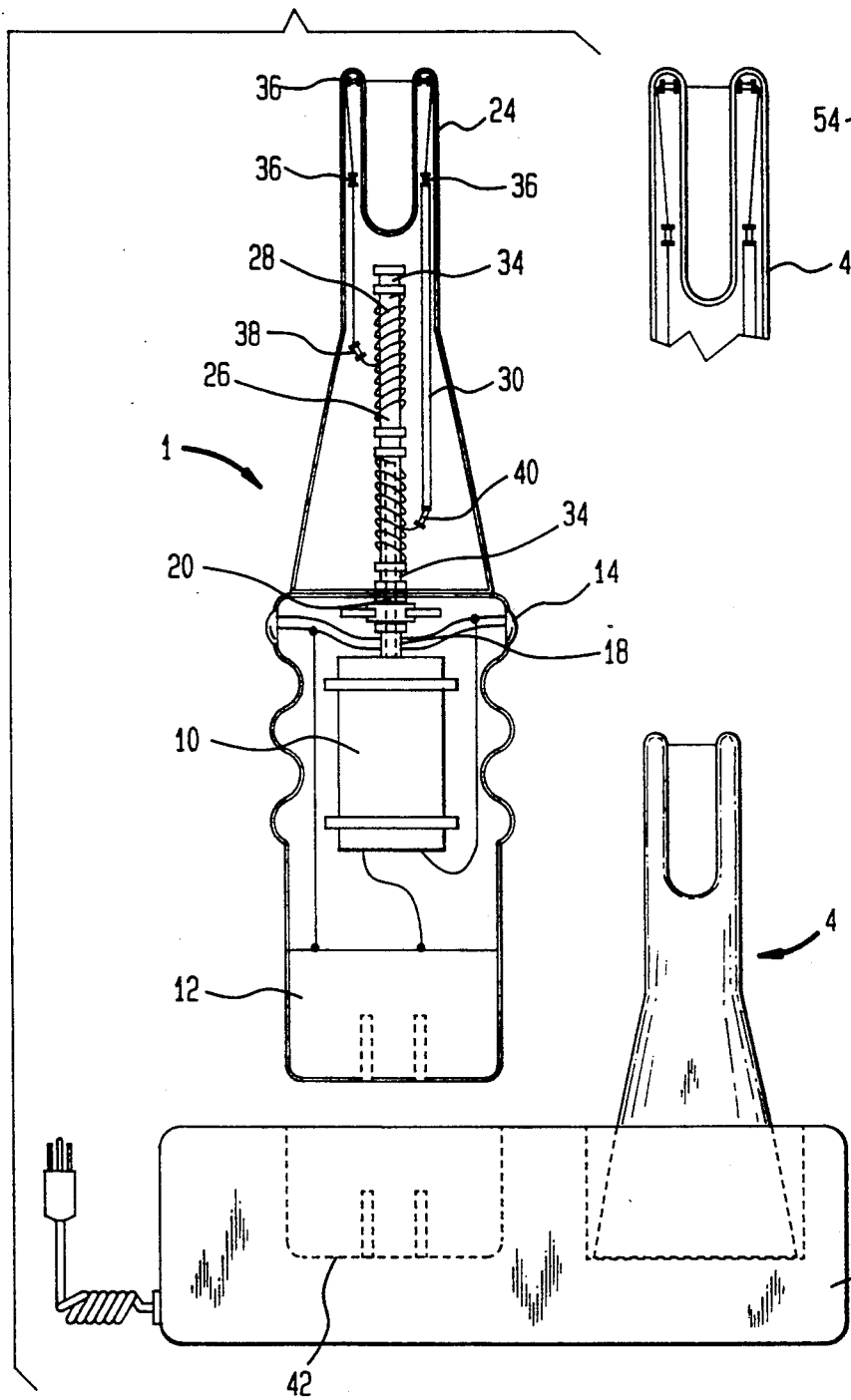

TEETH CLEANING APPARATUS

BACKGROUND OF THE INVENTION

1. Field of the Invention

The invention relates generally to a convenient teeth cleaning apparatus and methods of constructing and utilizing same. More particularly, the present invention relates to a power operated flossing device including a handle with a driving motor disposed therein, and one or more floss applicator units which can be easily, drivably connected to the handle. The floss applicator units have a desirably simple and inexpensive construction so that they may be disposed of after a period of use, and preferably are constructed in a variety of shapes, sizes and colors.

2. Description of Relevant Art

In the art there are known power operated flossing devices, including those disclosed in U.S. Pat. Nos. 4,245,658, 3,759,274, 3,534,745 and 3,421,524.

All of the known power operated flossing devices, however, suffer from various disadvantages. For example, the known devices cannot well accommodate many different users having significantly differently sized mouths and teeth arrangements, as well as the personal preferences of many users. Further, the known devices generally require some amount of manual manipulation of the floss relative to the device, such as moving a new section of floss into position on an applicator tip, installing a new spool of floss in the device, etc. Additionally, many of the known devices restore the floss therein after it has been used, which is not hygienic because the used floss will likely have food particles and/or germs thereon. Still further, many of the known devices are relatively complex and/or expensive.

SUMMARY OF THE INVENTION

The present invention has been designed to overcome the above discussed shortcomings and disadvantages of known power operated flossing devices.

According to the present invention there is provided teeth cleaning apparatus comprising handle means having a casing and a motor disposed therein, and floss applicator means which is adapted to be selectively, drivably connected to the handle means. The floss applicator means includes a casing with an applicator tip, a floss tube rotatably disposed within the applicator casing and having a quantity of floss provided thereon, while the motor has an output shaft which projects outwardly of the handle casing and is adapted to be securely, coaxially received within one end of the floss tube when the floss applicator means is connected to the handle means such that the flossing tube will rotate together with the output shaft when the motor is actuated. The quantity of floss is wound around a first portion of the floss tube in one direction, while an end portion of the floss extends along a path of movement from the first portion of the floss tube through the applicator tip to a second portion of the floss tube around which it is wound in a direction opposite to the one direction so that rotation of the floss tube advances the floss along the movement path from the first portion of the floss tube to the second portion of the floss tube.

Preferably the teeth cleaning apparatus will include a plurality of the floss applicator means, each of which may be selectively attached to the handle means as desired, and each of which may have an applicator tip which is shaped differently than the applicator tips of other applicator means. Additionally, the floss applicator means will preferably include means for guiding the floss along the movement path, means for tensioning the floss as it extends between the first and second portions of the floss tube, and means for sanitizing the floss as it is moved along a portion of the movement path between the applicator tip and the second portion of the floss tube.

It is an object of the present invention to provide a highly versatile, power operated flossing device which can be properly, favorably and conveniently utilized by many different users having differently sized mouths, different teeth arrangements, and different personal preferences, for thus encouraging maximum use.

It is another object of the present invention to provide such a device which includes a reusable handle portion which contains the expensive components of the device, including a motor, a switch and a power source, and a plurality of inexpensive floss applicator units/cartridges, each of which can be readily connected/disconnected to the handle portion as desired, and each of which is disposable after a quantity of floss provided therein has been utilized.

Still another object of the present invention is to provide such a device having a plurality of floss applicator units/cartridges having differently shaped applicator tips and/or different types of floss provided therein.

Yet another object of the present invention is to provide such a device in which the disposable floss applicator units/cartridges include means for sanitizing used floss which is stored therein.

Other objects, advantages and salient features of the present invention will become apparent from the following detailed description, which when taken into conjunction with the annexed drawings discloses a preferred embodiment of the invention.

BRIEF DESCRIPTION OF THE DRAWINGS

FIG. 1 is a front view of a power operated flossing device according to a preferred embodiment of the invention, the view showing a floss applicator unit mounted on the handle unit.

FIG. 2 is a side view of FIG. 1.

FIG. 3 is a front cross-sectional view of the device shown in FIG. 1, FIG. 3 also showing a storage tray for the flossing device and a second floss applicator unit supported by the storage tray.

FIGS. 4a and 4b are cross-sectional views of differently shaped applicator tip portions of two different floss applicator units.

DETAILED DESCRIPTION OF THE PREFERRED EMBODIMENTS

Figures 5, 6:
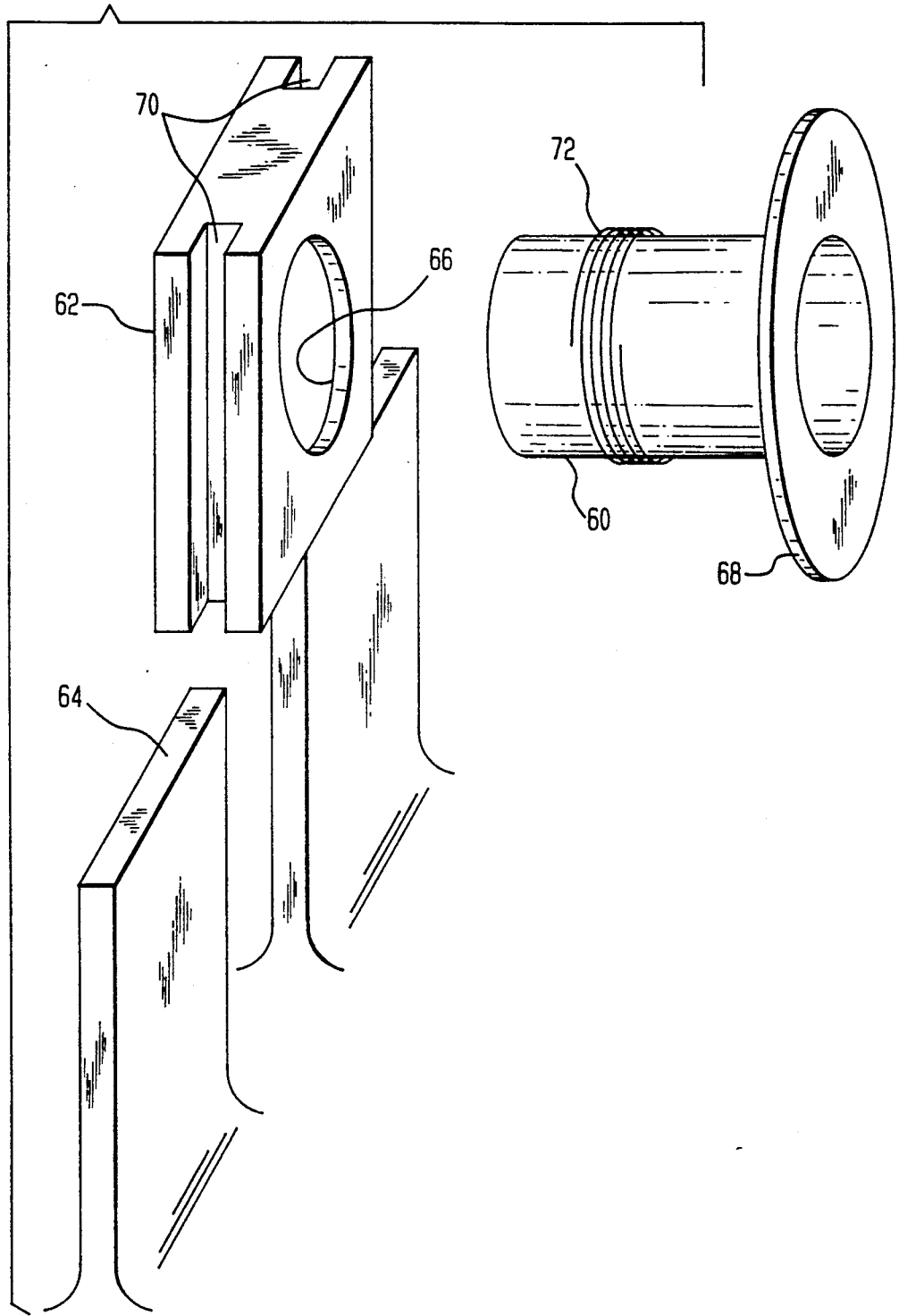
FIG. 5 shows a bushing construction for use in the power operated flossing device of FIG. 1.
FIG. 6 shows a modified floss construction which may be used in the power operated flossing device of FIG. 1.

Referring to FIGS. 1-3, a power operated flossing device according to the present invention is generally indicated at 1. The flossing device 1 includes a handle unit 2, a floss applicator unit 4, and a storage and recharging tray 6 as the three primary components thereof.

The handle unit 2 comprises a handle casing 8, an electric motor 10, a power source for the motor such as the rechargeable battery 12 shown in FIG. 3 and an actuator switch 14 which permits an operator to selectively actuate the motor 10.

The handle casing 8 is preferably constructed of molded plastic or the like and has a hand grip 16 integrally formed therein. As depicted, the hand grip 16 may simply consist of a series of alternating recesses and ridges formed in side surfaces of the casing 8. The motor 10 is preferably a direct drive, slow moving, high torque motor fixed within the casing 8 and has a rotatable output shaft 18 which projects out of the casing 8. A bushing 20 rotatably supports a portion of the output shaft 18 where it projects out of the casing 8, and also seals the opening in the casing against entry of foreign matter.

The actuator switch 14 preferably comprises a pair of push button type switches provided near the end of the handle unit 2 from which the motor output shaft 18 projects so that the switch 14 can be easily actuated by the thumb and/or forefinger of an operator's hand as it grips the handle unit 2. Preferably the switch will only rotate the motor 10 in a single (forward) direction. Also, as can be appreciated from FIGS. 1 and 2, the handle case 8 with the integral hand grip 16 and push button switch 14 has an attractive appearance.

The floss applicator unit 4 comprises an applicator casing 22 with an applicator tip 24 at an upper end thereof, a floss tube 26 rotatably supported within the applicator housing 22, a quantity of dental floss 28, a sanitizing means 30, and a lock mechanism 32.

The applicator casing 22 is preferably constructed of molded plastic or the like and is adapted to have one end thereof coupled to the end of the handle unit from which the motor output shaft 18 projects. More particularly, a flat face of the applicator casing 22 is adapted to flushly engage a corresponding flat face of the handle case 8, while simultaneously the projecting motor output shaft 18 is securely, tightly received within one end of the floss tube 26, as discussed further hereinbelow. Additionally, after the applicator unit 4 is engaged together with the handle unit 2, the locking mechanism 32 is manipulated to securely lock the units 2, 4 together in engaging relation. The locking mechanism 32 may simply comprise a sliding latch which is movable between a latched position and an unlatched position. Optionally, the locking mechanism 32 may include a biasing member, such as a leaf spring, for normally urging the sliding latch toward a latched position so that the mechanism 32 will automatically lock the units 2, 4 together, and an operator will simply have to slide the latch toward the unlocked position thereof whenever the operator desires to remove the applicator unit 4 from the handle unit 2. Also, the lock mechanism 32 may alternatively be provided on the handle unit 2 to minimize the cost of the floss applicator unit 4.

The floss tube 26 is preferably a simple, hollow plastic tube which is rotatably supported within the applicator case 22 by at least two bushings 34 such that the tube 26 is coaxially aligned with the opening in the flat engagement surface of the case 22 so that it can securely, coaxially receive the motor output shaft 18 therein, as discussed above. In the depicted embodiment three of the bushings 34 are preferably utilized, including a pair of the bushings supporting opposite ends of the floss tube 26, and a third bushing supporting a central portion of the tube. The bushing 34 disposed at the end of the tube 26 near the opening in the case 22 also functions to seal the opening against entry of foreign matter. The structure of each of the bushings 34 is more particularly shown in relation to FIG. 5, and will be discussed further hereinbelow.

A quantity of the dental floss 28 is wound in one direction about a first/upper portion of the floss tube 26 defined between two of the bushings 34, while an end portion of the floss 28 extends along a path of movement from the first portion of the floss tube 26 through the applicator tip 24 and back down to a second/lower portion of the floss tube 26, again defined between two bushings 34, around which it is wound in the direction opposite to the one direction. Through such arrangement of the floss 28 and the floss tube 26, upon actuation of the apparatus by switch 14, clockwise rotation of the floss tube 26 (as depicted in FIG. 3) will unwind a section of the floss from the upper portion of the tube 26, advance the floss along a path of movement, and wind an advancing section of the floss around the second portion of the floss tube 26. As will be understood, a large quantity of new dental floss 28 will initially be wound around the first portion of the tube 26 while a small end section of the floss will be extended through the path of movement and would around the second portion of the tube 26. Then as the flossing device is utilized over a period of time the large quantity of new floss 28 will be incrementally advanced along the path of movement by a person or persons utilizing the flossing device until it is substantially fully wound around the lower portion of the tube 26, at which time the applicator unit 4 may be simply disposed of and replaced with a new applicator unit.

The applicator unit 4 preferably includes a plurality of smaller bushings 36, 38, 40 for guiding the floss 28 along the path of movement from the first portion of the floss tube 26 to the second portion of the tube. The bushings 36 are substantially similar in construction to the larger bushings 34 except that they are smaller in size, while the bushings 38, 40 are also similar to the larger bushings 34 except that they include biasing members (such as coil springs) for restricting rotating movements thereof and for tensioning a section of the floss 28 extended between the first and second portions of the floss tube 26. As depicted in FIG. 3, the applicator unit 4 preferably includes four of the bushings 36, a single bushing 38, and a single bushing 40. Two of the bushings 36 are provided in confronting relation in opposite forks of the applicator tip 24, with each of such bushings 36 being provided adjacent to a floss opening defined in the corresponding fork of the applicator tip.

The sanitizing tube 30 is secured between one of the bushings 36 and the bushing 40, while its inner surface is coated with an appropriate anti-bacterial and deodorizing material. In use, used floss 28 passes through the tube 30 and contacts the anti-bacterial and deodorizing material in the tube before it is wound onto the second portion of the floss tube 26. The floss applicator unit 30 thus avoids hygiene problems associated with restoring used floss, which may contain food bits and germs, therein. As depicted, the tube 30 is preferably significantly longer than a distance between the forks of the applicator tip 24 so that a used section of the floss 28 will normally be stationarily disposed within the tube 30 for a period of time, i.e., at least the amount of time between successive actuations of the switch 14 by a user.

As shown by the dotted lines in FIG. 2, the applicator tip 24 may be pivotally connected to the applicator case 22 so that it may be freely pivoted between various positions as desired by persons utilizing the flossing device.

Referring to FIGS. 4a and 4b there are shown cross-sectional views of two differently sized applicator tips 44, 54 which can be utilized on a floss applicator unit according to the invention. As depicted, the applicator tip 44 has a smaller width between the forks thereof than the width between the forks of the applicator tip 54. Correspondingly, persons having smaller sized teeth, such as children, may prefer to use an applicator unit having a smaller sized tip such as the tip 44 whereas persons having larger size teeth may prefer to use an applicator unit having a larger sized applicator tip such as the tip 54. It is contemplated that the floss applicator units according to the present invention may have many differently sized and differently shaped applicator tips, and correspondingly it will be understood that the two tips shown in FIGS. 4a, 4b are merely illustrative of the fact that the applicator unit may come with many differently sized and shaped applicator tips.

Referring to FIG. 3 the power operated flossing device according to the present invention preferably includes the storage tray 6 for storing the handle unit 2 and one or more of the applicator units 4. As depicted, the storage tray 6 will preferably include a charging unit 42 which recharges the battery 12 in the handle unit 2 whenever it is stored in the tray 6. Although a rechargeable battery power source is depicted in the preferred embodiment, it will be understood that the handle unit 2 could alternatively include a power cord which would be plugged into an electrical outlet as desired. Similarly, although the storage tray 6 is depicted as storing only a single spare applicator unit 4, it will be understood that the tray could store any number of spare applicator units 4, and that the spare applicator units could have differently sized and shaped applicator tips, and could also be differently colored to designate different family members, for example.

Referring to FIG. 5 there is shown a preferred bushing construction according to the invention which would be utilized in each of the bushings 34, 36, 38 and 40. The bushing mechanism includes three primary components, a tubular bushing 60, a retainer 62 and a mounting bracket 64, all of which are preferably constructed of plastic. The bushing 60 is a tubular member having a diameter which is slightly smaller than the diameter of a central opening 66 defined in the retainer 62 so that when the bushing 60 is inserted through the opening 66 it can freely rotate therein. One end of the bushing will preferably have a flange 68 preformed thereon, such as during an initial molding of the bushing, and after the bushing is inserted through the opening 66 the opposite end of the bushing 60 will also be flared out, such as through the application of heat, so that the bushing will be rotatably secured to the retainer. The retainer 62 also has a pair of grooves 70 defined in opposite side surfaces thereof, which grooves 70 are adapted to securely engage the bracket 64 when the retainer 62 is pushed down onto the bracket 64, for thus securing the bushing 60 in place. It is preferred that all of the brackets 64 be formed or molded integrally with the applicator case 22 such that the brackets project inwardly from an inner surface of the case 22 in all the appropriate positions, whereby accurate assembly of the bushings in the case 22 is highly simplified. Thus, the bushing mechanism comprises three simple, molded plastic components 60, 62, 64, and thus can be easily and inexpensively manufactured and assembled, and yet functions very effectively in accurately securing various components (the floss tube 26, the sanitizing tube 30 and the floss 28) within the applicator unit 4.

Also depicted in FIG. 5 is a biasing member or spring 72. A pair of such springs 72 may be disposed between the respective flanges 68 on opposite ends of the bushing 60 and opposite, engaging surfaces of the retainer 62, such as shown in relation to the bushings 38, 40 of FIG. 3. In use the springs 72 restrict rotation of bushing 60 within the retainer 62, and also function to tension a section of floss extending between the bushings 38, 40.

The bushing 20 in the handle unit 2 will preferably also have a construction such as shown in FIG. 5.

Referring to FIG. 6, there is shown a modified dental floss 88 which may be utilized in the apparatus 1 according to the invention. The modified floss 88 has nodes 90 provided in a spaced, repeating pattern along the length thereof, which nodes 90 are very effective in dislodging food particles stuck between teeth.

As will be understood from all of the foregoing discussion, the floss applicator unit 22 has a relatively simply construction, and is preferably composed substantially entirely of plastic. Because of such construction, the floss applicator unit 22 can be manufactured as an inexpensive, disposable unit which can be easily, selectively connected to the handle unit 2 as desired, and can be conveniently disposed of once the quantity of floss 28 therein has been fully utilized.

Although there has been described what is at present considered to be the preferred embodiment of the present invention, it will be understood that the invention can be embodied in other specific forms without departing from the spirit or essential characteristics thereof. For example, although the floss applicator units 4 are intended to be disposable, it is contemplated that they may be reusable such that a new quantity of floss or a new floss tube with new floss could be installed therein. The present embodiment is, therefore, to be considered in all aspects as illustrative, and not restrictive.

The scope of the invention is indicated by the appended claims rather than by the foregoing description.

I claim:

1. Teeth cleaning apparatus, comprising:
    handle means having a casing with a motor disposed therein; and
    floss applicator means adapted to be selectively, drivably connected to said handle means;
    said floss applicator means including a casing with a floss applicator tip, a floss tube rotatably disposed within said applicator casing and having a supply of new floss provided thereon;
    said motor having a rotatable output shaft which projects outwardly of said handle casing and is adapted to be securely, coaxially received within one end of said floss tube when said floss applicator means is connected to said handle means such that said floss tube will rotate together with said output shaft when said motor is actuated;
    said supply of new floss being wound around a first portion of said floss tube in one direction, and one end of said new floss being extended along a path of movement through said applicator tip to a second portion of said floss tube around which said floss is wound in a direction opposite to said one direction, such that used floss will be taken up by said second portion of said floss tube;
    said applicator means further including means for sanitizing said used floss as it is moved along a section of said path of movement between said applicator tip and said second portion of said floss tube; and said sanitizing means comprising a tube lined with an anti-bacterial substance, said floss extending through said sanitizing tube.

2. Teeth cleaning apparatus according to claim 1, wherein said floss applicator means further includes bushing means for guiding said floss along said path of movement.

3. Teeth cleaning apparatus according to claim 2, wherein said bushing means comprises a plurality of bushings, each said bushing being secured to an inner surface of said applicator casing.

4. Teeth cleaning apparatus according to claim 3, wherein said applicator casing is formed integrally with a plurality of bushing holders as a unitary member, said bushing holders projecting inwardly from said inner surface of said applicator casing.

5. Teeth cleaning apparatus according to claim 3, wherein said applicator casing, said bushing means, and said floss tube are all constructed substantially entirely of plastic.

6. Teeth cleaning apparatus according to claim 2, wherein said bushing means includes means for tensioning a section of said floss extending between said first and second portions of said floss tube.

7. Teeth cleaning apparatus according to claim 1, wherein said floss applicator means further includes first bushing means for guiding said floss along said path of movement and second bushing means for rotatably supporting said floss tube within said applicator casing.

8. Teeth cleaning apparatus according to claim 7, wherein each of said first and second bushing means comprises a plurality of bushings, and each said bushing is secured to an inner surface of said applicator casing.

9. Teeth cleaning apparatus according to claim 8, wherein said applicator casing is formed integrally with a plurality of bushing holders as a unitary member, said bushing holders projecting inwardly from said inner surface of said applicator casing.

10. Teeth cleaning apparatus according to claim 8, wherein said applicator casing, said floss tube, said first bushing means and said second bushing means are all constructed substantially entirely of plastic.

11. Teeth cleaning apparatus according to claim 1, wherein said supply of new, unused floss has a plurality of nodes provided therealong in a repeating pattern.

12. Teeth cleaning apparatus, comprising:

handle means having a casing with a motor disposed therein; and floss applicator means adapted to be selectively, drivably connected to said handle means;

said floss applicator means including a casing with a floss applicator tip, a floss tube rotatably disposed within said applicator casing and having a quantity of floss provided thereon;

said motor having a rotatable output shaft which projects outwardly of said handle casing and is adapted to be securely, coaxially received within one end of said floss tube when said floss applicator means is connected to said handle means such that said floss tube will rotate together with said output shaft when said motor is actuated;

said applicator means further including means for sanitizing said floss as it is moved along a section of said path of movement between said applicator tip and said second portion of said floss tube; and said sanitizing means comprises a tube lined with an anti-bacterial substance, said floss extending through said sanitizing tube.

13. Teeth cleaning apparatus according to claim 12, including means for selectively locking said handle means to said floss applicator means after the handle means and the floss applicator means have been connected together.

14. Teeth cleaning apparatus according to claim 12, including switch means for selectively actuating said motor to rotate said floss tube, and said handle case has a hand grip defined integrally therein.

15. Teeth cleaning apparatus according to claim 12, wherein said applicator tip is pivotally secured to one end of said applicator casing.

16. Teeth cleaning apparatus according to claim 12, including a plurality of said floss applicator means, each said floss applicator means is adapted to be independently, selectively, drivably connected to said handle means.

17. Teeth cleaning apparatus according to claim 16, wherein each said applicator means includes a casing with an applicator tip which is shaped differently than an applicator tip of another said applicator means.

18. Teeth cleaning apparatus according to claim 16, including a storage tray for storing said handle means and said plurality of floss applicator means when not in use; and power supply means for said motor.

* * * * *

UNITED STATES PATENT AND TRADEMARK OFFICE
CERTIFICATE OF CORRECTION

PATENT NO. : 5,207,773
DATED : May 4, 1993
INVENTOR(S) : Doug Henderson

It is certified that error appears in the above-identified patent and that said Letters Patent is hereby corrected as shown below:

Column 4, line 22, change "would" to --wound--.

Signed and Sealed this

Twenty-eighth Day of December, 1993

Attest:

BRUCE LEHMAN

Attesting Officer

Commissioner of Patents and Trademarks